US008168196B2

(12) United States Patent
Watanabe et al.

(10) Patent No.: US 8,168,196 B2
(45) Date of Patent: May 1, 2012

(54) ***GRIFOLA FRONDOSA*-DERIVED SUBSTANCE HAVING ANTI-INFLUENZA VIRUS ACTIVITY AND METHOD FOR PRODUCING THE SAME**

(75) Inventors: Masataka Watanabe, Utsunomiya (JP); Masahide Takeyama, Saitama (JP)

(73) Assignee: Yukiguni Maitake Co., Ltd., Niigata (JP)

( * ) Notice: Subject to any disclaimer, the term of this patent is extended or adjusted under 35 U.S.C. 154(b) by 334 days.

(21) Appl. No.: 12/447,212

(22) PCT Filed: Oct. 26, 2007

(86) PCT No.: PCT/JP2007/071356
§ 371 (c)(1),
(2), (4) Date: Apr. 24, 2009

(87) PCT Pub. No.: WO2008/050910
PCT Pub. Date: May 2, 2008

(65) Prior Publication Data
US 2010/0239602 A1 Sep. 23, 2010

(30) Foreign Application Priority Data

Oct. 27, 2006 (JP) .................................. 2006-292091

(51) Int. Cl.
*A61K 35/84* (2006.01)
(52) U.S. Cl. .................................................. 424/195.15
(58) Field of Classification Search .................. None
See application file for complete search history.

(56) References Cited

U.S. PATENT DOCUMENTS

| 5,854,404 | A | * | 12/1998 | Nanba et al. | 530/424 |
|---|---|---|---|---|---|
| 6,616,928 | B1 | * | 9/2003 | Tazawa et al. | 424/195.15 |
| 6,783,771 | B2 | * | 8/2004 | Ikekawa et al. | 424/461 |
| 7,214,778 | B2 | * | 5/2007 | Zhuang et al. | 530/395 |
| 2003/0012798 | A1 | | 1/2003 | Ikekawa et al. | |
| 2004/0213856 | A1 | * | 10/2004 | Scheinbart | 424/568 |
| 2006/0171958 | A1 | * | 8/2006 | Stamets | 424/195.15 |
| 2007/0027069 | A1 | * | 2/2007 | Masuda et al. | 514/8 |

FOREIGN PATENT DOCUMENTS

| CN | 1416349 | A | | 5/2003 |
|---|---|---|---|---|
| EP | 0 893 449 | A1 | | 1/1999 |
| JP | 06 312934 | A | | 11/1994 |
| JP | 2005 132810 | A | | 5/2005 |
| JP | 2005-132810 | A | | 5/2005 |
| JP | 2005-145934 | | * | 6/2005 |
| JP | 2007-031665 | A | | 2/2007 |

OTHER PUBLICATIONS

The State Intellectual Property Office of the People's Republic of China, First Office Action, CN 200780047435.X, Dec. 13, 2010.
Masuda, et al., *Grifola frondosa* ganyu glycoprotein (MZ-Fraction) no in vitro ni okeru macrophage J774.1 saibo no kasseika, Proceedings of the Annual Meeting of the Pharmaceutical Society of Japan, 2005, vol. 125th(3), p37.
Zhuang, et al., Studies on the host-mediated antitumor polysaccharides part XVIII. The detailed fractionation and antitumor activity of the mycelial polysaccharides from liquid cultured *Grifola frondosa* fungus, Reports of the Faculty of Agriculture, Shizuoka University, 1993, vol. 42, pp. 43-58.

* cited by examiner

*Primary Examiner* — Christopher R. Tate
(74) *Attorney, Agent, or Firm* — Lucas & Mercanti, LLP (57) ABSTRACT

This invention is intended to discover a fraction having strong anti-influenza virus activity via Mφ activation in the *Grifola frondosa* extract or an active substance distributed therein to develop a simple and effective production method and to use such fraction for food and beverage products, pharmaceutical products, feeds or feed additives, and the like. This is realized by treatment of maitake mushrooms with a molecular sieve apparatus, such as an ultrafiltration apparatus or gel filtration apparatus, to isolate glycoprotein-containing fractions or sugar-protein complex-containing fractions having molecular weights of 30,000 to 100,000, so as to minimize the influence on substances having strong anti-influenza virus activity and contaminants.

7 Claims, 4 Drawing Sheets

Concentration of extracted fraction added to Mφ medium (b)

Concentration of extracted fraction added to Mφ medium

GRIFOLA FRONDOSA-DERIVED SUBSTANCE HAVING ANTI-INFLUENZA VIRUS ACTIVITY AND METHOD FOR PRODUCING THE SAME

This application is a 371 of PCT/JP/2007/071356 filed on Oct. 26, 2007, which claims the benefit of Japanese Patent Application No. 2006-292091 filed on Oct. 27, 2006, the contents of each of which are incorporated herein by reference.

TECHNICAL FIELD

The present invention relates to a given fraction extracted from *Grifola frondosa* having anti-influenza virus activity and a method for producing the same.

The present invention relates to a fraction containing a glycoprotein derived from *Grifola frondosa* having activity of inducing TNF-α synthesis or a fraction containing a sugar-protein complex and a method for producing the same.

Further, the present invention relates to food and beverage products, pharmaceutical products, feeds, or feed additives containing a fraction containing a glycoprotein derived from *Grifola frondosa* or a fraction containing a sugar-protein complex.

BACKGROUND ART

Influenza is a form of acute inflammation starting from virus growth in the throat or the upper respiratory mucous membrane caused by infection with influenza viruses (type A, type B, or type C). In addition to inflammation in the respiratory tract, constitutional symptoms, such as high fever, feebleness, headache, muscle ache, or arthralgia, develop. Healthy adults recover from such acute inflammation within approximately a week. People with an underlying disease, such as chronic lung disease, renal disease, heart disease, or diabetes, babies and toddlers, and elderly adults are high risk groups that are regarded as being at high risk of developing complications with pneumonia or other diseases (Hiroshi Ochiai, *Yakkyoku (Pharmacy)*, vol. 44, 1231-1237, 1993; Non-Patent Document 1).

In recent years, vaccines become known as influenza prevention measures at the social level, and the influenza vaccination coverage rate is increasing. Since the antigenicity of the influenza virus is likely to vary, effects of vaccines are not stable, and the initial effects cannot be always expected.

In addition to rapid diagnostic techniques, therapeutic agents are remarkably developed, and oseltamivir phosphate and the like are stocked in preparation for the flu season. However, the appearance of resistant viruses, side effects resulting from ingestion, and the like have been reported, and therapeutic drugs cannot be regarded as being problem-free. The present applicant considered that searching for of substances having anti-influenza virus activity from among naturally-occurring substances, which are safe and easily obtained, or extracts thereof would be significant in view of the dangerous nature of influenza. Thus, the present applicant has heretofore focused on mushrooms, which have been artificially cultivated in large quantities as food materials, and in particular, *Grifola frondosa* mushrooms, which have been reported to have immunostimulatory activity.

A variety of effects of *Grifola frondosa* extracts have been known because of development efforts made by the present applicant and others. For example, effects of ameliorating AIDS are reported in JP Patent Publication (kokai) No. H7-69913 (A) (1995) (Patent Document 1), anti-tumor effects are reported in JP Patent Publication (kokai) No. H9-238697 (A) (1997) (JP Patent No. 2859843; Patent Document 2), activity of eliminating active oxygen is reported in JP Patent Publication (kokai) No. 2000-119650 (A) (JP Patent No. 3260329; Patent Document 3), and activity of inducing NO production is reported in JP Patent Publication (kokai) No. 2001-172194 (A) (Patent Document 4).

The present inventors have conducted concentrated studies regarding the ingredients of *Grifola frondosa*. As a result, they discovered that a hot-water extract of *Grifola frondosa* had anti-influenza virus activity, and they filed a patent application (i.e., JP Patent Publication (kokai) No. 2005-145934 (A) (Patent Document 5). A discovery of bio-defense activity, such as anti-influenza virus activity, in extracted fractions of *Grifola frondosa* mushrooms, which are safe, mass-produced as food materials, is very significant.

It is demonstrated that the defense mechanism against infection; i.e., the immune system, involves phagocytosis via non-specific recognition (i.e., natural immunity or a non-specific defense mechanism) caused by macrophages (hereafter abbreviated as "Mφ") and the like upon infection with viruses or the like. It is also demonstrated that cytokines are released or antigens are presented on the cell surface, and helper T cells receive signals to activate a more sophisticated defense mechanism, when the viruses cannot be fully treated (i.e., acquired immunity or a specific defense mechanism). When the acquired immune system is activated, further, T cells, NK cells, and the like may be activated (i.e., cell-mediated immunity). Alternatively, B cells may be activated (i.e., humoral immunity). Based on the research conducted in the past, nature of a *Grifola frondosa* ingredient exhibiting anti-tumor activity has been demonstrated to be a β-D-glucan-type polysaccharide (i.e., a sugar component of a sugar-protein complex) having a special chemical structure (a β-1,6 main chain and β-1,3 side chains) (Chem. Pharm. Bull., 35 (3), 1162-1168, 1987, Non-Patent Document 2). Thereafter, *Grifola frondosa* ingredients having other chemical structures that exhibit excellent anti-tumor effects have not yet been discovered. Such action mechanism has been found to involve activation of the cell-mediated immune system that starts from activation of macrophages (Biol. Pharm. Bull., 25 (12), 1647-1650, 2002, Non-Patent Document 3).

In the past, the present applicant invented a sugar-protein complex (Patent Document 2), which was obtained by purifying a hot-water extract of *Grifola frondosa* mushrooms via alcohol treatment, and demonstrated that such sugar-protein complex was an anti-tumor substance having excellent immunostimulatory activity. The present inventors deduced that extracts of *Grifola frondosa* mushrooms having immunostimulatory activities starting from Mφ activation would provide useful actions in protection against virus infection. As a result of the research, they discovered that TNF-α would be released upon Mφ activation and that TNF-α would function as a virus proliferative inhibitory factor in cells infected with influenza viruses (Patent Document 5). This action takes place at the activation stage of the natural immune system, and drug resistance would not be caused in principle, unlike the action mechanism caused by vaccines. Thus, such action is considered to be significant immunostimulatory activity caused by a food component.

When excellent anti-tumor activity was first discovered in a sugar-protein complex (a sugar component is composed of β-D-glucan) contained in *Grifola frondosa*, giant macromolecules having molecular weights of about 1,000,000 or greater had been the subjects of focus. In general, substances having greater molecular weights are more likely to experience cleavage of molecular bonds during the process of purification, and purification of such substances without damage is likely to be difficult. Also, the amount of contaminants contained in an extract from naturally-occurring substances tends to increase in substances having lower molecular weights.

Patent Document 1: JP Patent Publication (kokai) No. H7-69913 (A) (1995)
Patent Document 2: JP Patent Publication (kokai) No. H9-238697 (A) (1997)
Patent Document 3: JP Patent Publication (kokai) No. 2000-119650 (A)
Patent Document 4: JP Patent Publication (kokai) No. 2001-172194 (A)
Patent Document 5: JP Patent Publication (kokai) No. 2005-145934 (A)
Non-Patent Document 1: Hiroshi Ochiai, *Yakkyoku* (*Pharmacy*), vol. 44, 1231-1237, 1993
Non-Patent Document 2: Chem. Pharm. Bull., 35 (3), 1162-1168, 1987
Non-Patent Document 3: Biol. Pharm. Bull., 25 (12), 1647-1650, 2002

DISCLOSURE OF THE INVENTION

The present invention is intended to discover a fraction having strong anti-influenza virus activity via Mφ activation in a *Grifola frondosa* extract or a fractionated region comprising active substances distributed therein to develop a simple and effective production method and to use such fraction or fractionated region for food and beverage products, pharmaceutical products, feeds or feed additives, and the like.

The present inventors have conducted concentrated studies in order to attain the above objects. As a result, they discovered that intermediate fractions having relatively low molecular weights in a hot-water extract of *Grifola frondosa* have anti-influenza virus activities superior to other components. This has led to the completion of the present invention.

The present inventors searched for extraction conditions that would provide small changes to substances having anti-influenza virus activity, that would produce low amounts of contaminants, and that would be able to determine the properties of substances more accurately than conventional techniques. Further, they extracted glycoprotein-containing fractions or sugar-protein complex-containing fractions having low molecular weights of 30,000 to 100,000 using a molecular sieve apparatus, such as an ultrafiltration apparatus or gel filtration apparatus, thereby completing the present invention.

Specifically, the present invention relates to the following:
(1) a method for producing a fraction extracted from *Grifola frondosa* comprising treating the fruit body or mycelia of *Grifola frondosa* with hot water, treating the resulting extract with a molecular sieve apparatus, and obtaining a fraction having a molecular weight distribution of 30,000 to 100,000;
(2) a method for producing a fraction extracted from *Grifola frondosa* comprising treating the fruit body or mycelia of *Grifola frondosa* with hot water, adding alcohol to the resulting extract, allowing the mixture to stand, removing substances and alcohol suspended on the liquid surface or in the liquid, treating the resultant with a molecular sieve apparatus, and obtaining a fraction having a molecular weight distribution of 30,000 to 100,000;
(3) a fraction extracted from *Grifola frondosa* having a molecular weight distribution of 30,000 to 100,000, which is produced by the method according to (1) or (2);
(4) a fraction extracted from *Grifola frondosa* having a molecular weight distribution of 30,000 to 100,000 produced by the method according to (1) or (2), the fraction comprising sugar and protein at a ratio of 50:50 to 65:35 and having positive color reactions with anthrone and ninhydrin;
(5) an active substance for inducing TNF-α production comprising the fraction extracted from *Grifola frondosa* according to (3) or (4);
(6) a substance having anti-influenza virus activity comprising the fraction extracted from *Grifola frondosa* according to (3) or (4);
(7) a food and beverage product comprising the fraction extracted from *Grifola frondosa* according to any of (3) to (6);
(8) a pharmaceutical product comprising the fraction extracted from *Grifola frondosa* according to any of (3) to (6); and
(9) a feed or feed additive comprising the fraction extracted from *Grifola frondosa* according to any of (3) to (6).

Examples of *Grifola frondosa* mushrooms that can be used in the present invention include *Grifola albicans*, *Dendropolyporus umbellatus*, and *Grifola gigantia*. Also, fruit bodies or mycelia of such *Grifola frondosa* mushrooms can be used. In recent years, artificial cultivation of the fruit body of *Grifola frondosa* became available, and use of the fruit body of *Grifola frondosa* is preferable from the viewpoint of stable acquisition of starting materials.

Fresh, dry, or dry powder of *Grifola frondosa* may be used, and dry powder is preferable in terms of handleability. Dry *Grifola frondosa* may be obtained by sun-drying, hot-air drying, lyophilization, or other means. Dry powder of *Grifola frondosa* may have coarse to fine grain sizes.

Extraction is carried out with the use of hot water. The term "hot water" used herein refers to water at 60° C. or higher. The term "water" refers to tap water or pure water, such as deionized water (ion exchanged water), distilled water, or water obtained through reverse osmosis. Accordingly, extraction can be adequately carried out in accordance with a conventional technique by mixing *Grifola frondosa* with water with heating at an ordinary to pressurized state. For example, extraction is carried out at 60° C. to 125° C. for 5 minutes to several hours. In order to effectively perform extraction within a short period of time, extraction may be carried out at 100° C. or higher; for example, extraction may be carried out with the use of an autoclave under pressure at around 120° C. for approximately 30 minutes to 1 hour.

The obtained extract is cooled to room temperature, ethanol is added to a final concentration of 50% therein, the mixture is allowed to stand at 10° C. or lower overnight, solid substances suspended on the liquid surface or in the liquid are removed, and ethanol is removed with the use of a vacuum distillator. Thus, a brown extract can be obtained.

The thus-obtained extract is treated with the use of a molecular sieve apparatus. An ultrafiltration apparatus, a gel filtration apparatus, or the like is used as a molecular sieve apparatus.

As an ultrafiltration apparatus, commercially available apparatuses, such as a pressure agitation-based apparatus, a hollow fiber filter-based apparatus, a cassette system-based apparatus, a thin-channel system-based apparatus, or a vacuum suction-based apparatus, can be adequately used. As ultrafiltration membranes, for example, a cellulose acetate, cellulose, oxidized cellulose, polyether sulfone, polysulfone, polysaccharide, or vinyl acrylic copolymer membrane having a molecular weight cut off of 30,000 is used in combination with a membrane having molecular weight cut off of 100,000.

A membrane with a molecular weight cut off of 100,000 is first used to collect fractions having molecular weights of 100,000 or less and a membrane with a molecular weight cut off of 30,000 is then used to remove fractions having molecular weights of 30,000 or less to obtain fractions having molecular weights of 30,000 to 100,000.

Alternatively, a membrane with a molecular weight cut off of 30,000 may be first used to collect fractions having molecular weights of 30,000 or greater and a membrane with a molecular weight cut off of 100,000 may then be used to remove fractions having molecular weights of 100,000 or greater to obtain fractions having molecular weights of 30,000 to 100,000.

Gel filtration can separate substances having arbitrary molecular weights via chromatography separation in accordance with different molecular sizes of solutes. Dextran-based sephadex, agarose, cellulose, and other common gels can be used.

For example, dry powder of the fruit body of *Grifola frondosa* and an adequate amount of water are introduced into an autoclave, extraction is carried out under pressure at 115° C. to 120° C., and the residue is removed using a general filter apparatus such as a filter press to obtain an extract. The resulting extract is directly applied to an ultrafiltration apparatus or gel filtration apparatus or optionally subjected to alcohol precipitation, which is a purification means for polymeric polysaccharides, or it undergoes other treatment to remove giant macromolecular substances with molecular weights of several hundreds of thousands to fractionate low-molecular-weight fractions having molecular weights of 30,000 to 100,000. The removed polymeric substances can be used separately.

The thus-obtained low-molecular-weight fraction is brown liquid, such liquid is concentrated to obtain an essence, the essence is further dried, and the resultant can be used as extract powder. Dry extract powder is easy to handle, and such dry extract powder can be obtained by spray drying, lyophilization, or other means. The dry extract powder of fractions having molecular weights of 30,000 to 100,000 thus obtained is light-brown powder, the ratio of sugar to protein is between 50:50 and 65:35, and color reactions are positive with anthrone and ninhydrin. Proteins were found to be composed of glutamic acid, asparatic acid, alanine, lysine, valine, arginine, threonine, glycine, serine, leucine, proline, isoleucine, phenylalanine, tyrosine, histidine, tryptophan, cystine, methionine, and the like via automatic amino acid analysis (tryptophan was analyzed via high-performance liquid chromatography). Such amino acid constitution was consistent with the constitution described in the invention, which had been made by the present applicant in the past (Patent Document 2).

The *Grifola frondosa*-derived fractions having molecular weights of 30,000 to 100,000 of the present invention were added in amounts of 100 μg/ml of medium of mouse-derived macrophage P388D1 cells, culture was conducted for various periods of time, the obtained culture supernatants were added to a medium of canine kidney renal epithelial (P388D1) cells, which had been infected with influenza virus in advance, and culture was then conducted for 24 hours. The *Grifola frondosa* extract, which existed prior to treatment with a molecular sieve apparatus (hereafter, such fraction is referred to as an "unfractionated extract"), was designated as a control. As a result, activity of influenza virus growth inhibition was found to be stronger when fractions having molecular weights of 30,000 to 100,000 were added than when unfractionated extracts or other fractions were added, as is apparent from the results described in "<Test Example> Examination of anti-influenza virus activity" below.

The above results demonstrate that *Grifola frondosa*-derived fractions having molecular weights of 30,000 to 100,000 have excellent anti-influenza virus activities and that such fractions can be incorporated into food and beverage products, pharmaceutical products, and feeds or feed additives for prevention of the common cold, such as influenza virus, or for alleviation of symptoms after infection.

The term "food and beverage product" used herein refers to, for example, beverage products, such as milk and drinks, various processed food products that are routinely eaten, so-called health food products, such as nutritional supplementary food, dietary supplements, other supplements, health-promoting foods, including food with nutrient function claims and food for specified health use, and special-use foods, including foods for aged individuals. Pharmaceutical products include animal drugs.

When the *Grifola frondosa*-derived fractions are used for health food products, supplements, food with health-promoting benefits, pharmaceutical products, or pharmaceutical products for animals, excipients and extenders may be adequately added to prepare various types of pharmaceutical preparations, such as tablets, capsules, granules, powders, pills, liquid preparations, or suspensions.

When the *Grifola frondosa*-derived fractions are used for feeds or feed additives, the fractions may be fed to animals in that state or may be adequately incorporated into various feeds. The fractions can be dissolved in drinking water and fed to animals.

This description includes part or all of the contents as disclosed in the description and/or drawings of Japanese Patent Application No. 2006-292091, which is a priority document of the present application.

BEST MODES FOR CARRYING OUT THE INVENTION

Hereafter, examples are provided so as to describe the present invention in detail, although the present invention is not limited thereto.

Example 1

Powder of dried fruit bodies of *Grifola frondosa* (10 kg) and 120 l of water were introduced into an autoclave, extraction was carried out under pressure at 120° C. for 30 minutes, and the residue was removed using a filter press to obtain 93 l of an extract (concentration: 4%). The extract was concentrated to a concentration of 10% using a vacuum distillator to obtain 37 l of a dark brown extract. The extract was filtered through a membrane filter (0.45 μm), 400 ml of unfractionated extract was filtered through a cross-flow ultrafiltration membrane unit (Vivaflow 50; molecular weight cut off of 100,000, Vivascience Ltd.), and 360 ml of filtrate and 40 ml of unfiltered solution were obtained. Water (360 ml) was added to the unfiltered solution, the resultant was filtered again, and 360 ml of filtrate and 40 ml of unfiltered solution were obtained. The same procedure was repeated two more times, and unfiltered solutions; i.e., 40 ml of a fraction having a molecular weight of 100,000 or greater and 1,440 ml of a fraction having a molecular weight of 100,000 or less composed of filtrates resulting from 4 filtration operations, were obtained in the end. The latter was concentrated to 400 ml using an evaporator.

The fraction having a molecular weight of 100,000 or less (400 ml) was filtered using an ultrafiltration membrane unit (Vivaflow 50; molecular weight cut off of 30,000, Vivascience Ltd.), and 360 ml of filtrate and 40 ml of unfiltered solution were obtained. Water (360 ml) was added to the unfiltered solution, the resultant was subjected to ultrafiltration again, and 360 ml of filtrate and 40 ml of unfiltered solution were obtained. The same procedure was repeated two more times, and unfiltered solutions; i.e., 40 ml of a fraction having a molecular weight of 30,000 to 100,000 and 1,440 ml of a fraction having a molecular weight of 30,000 or less composed of filtrates resulting from 4 filtration operations, were obtained in the end. The latter was concentrated to 400 ml using an evaporator.

The thus-obtained unfractionated extract was dried using a spray drier, and the extracted fractions were lyophilized. Consequently, a brown unfractionated extract, 1.1 g of a canescent fraction having a molecular weight of 100,000 or greater, 2 g of a light brown fraction having a molecular weight of 30,000 to 100,000, and 36 g of a brown fraction having a molecular weight of 30,000 or less were obtained.

Example 2

Powder of dried fruit bodies of Grifola frondosa (20 kg) and 230 l of water were introduced into an autoclave, extraction was carried out under pressure at about 120° C. for about 30 minutes, and the residue was removed using a filter press to obtain 200 l of an extract (concentration: 4%). The extract was concentrated using a vacuum distillator to obtain 31 l of a brown extract (concentration: 22%). The brown liquid was cooled to room temperature, 95% ethanol was added to a final concentration of 50% therein, and the mixture was allowed to stand at 10° C. or lower overnight. Solid substances suspended on the liquid surface or in the liquid were removed, and ethanol was removed and concentrated with the use of a vacuum distillator to obtain 16 l of an extract (concentration: 42%). The extract was spray-dried using a spray drier to obtain an extract of Grifola frondosa.

The extract of Grifola frondosa (30 g) was dissolved in water and filtered through a membrane filter (0.45 μm) to obtain 400 ml of a brown unfractionated extract. The unfractionated extract was filtered through a cross-flow ultrafiltration membrane unit (Vivaflow 50; molecular weight cut off of 100,000, Vivascience Ltd.), and 360 ml of filtrate and 40 ml of unfiltered solution were obtained. Water (360 ml) was added to the unfiltered solution, the resultant was subjected to ultrafiltration again, and 360 ml of filtrate and 40 ml of unfiltered solution were obtained. The same procedure was repeated one more time, and unfiltered solutions; i.e., 40 ml of a fraction having a molecular weight of 100,000 or greater and 1,080 ml of a fraction having a molecular weight of 100,000 or less composed of filtrates resulting from 3 filtration operations, were obtained. The latter was concentrated to 400 ml using an evaporator.

The fraction having a molecular weight of 100,000 or less (400 ml) was filtered using an ultrafiltration membrane unit (Vivaflow 50; molecular weight cut off of 30,000, Vivascience Ltd.), and 360 ml of filtrate and 40 ml of unfiltered solution were obtained. Water (360 ml) was added to the unfiltered solution, the resultant was subjected to ultrafiltration again, and 360 ml of filtrate and 40 ml of unfiltered solution were obtained. The same procedure was repeated one more time, and unfiltered solutions; i.e., 40 ml of a fraction having a molecular weight of 30,000 to 100,000 and 1,080 ml of a fraction having a molecular weight of 30,000 or less composed of filtrates resulting from 3 filtration operations, were obtained. The latter was concentrated to 400 ml using an evaporator.

The thus-obtained extracted fractions were lyophilized. Consequently, 0.78 g of a canescent fraction having a molecular weight of 100,000 or greater, 1.4 g of a light brown fraction having a molecular weight of 30,000 to 100,000, and 27 g of a brown fraction having a molecular weight of 30,000 or less were obtained.

The properties of the target fraction of the present invention having molecular weights of 30,000 to 100,000 thus obtained are described.

Appearance: Light brown powder
Color reaction: Positive with the anthrone reaction and the ninhydrin reaction
Molecular weight: 30,000 to 100,000
Organic component: Mainly carbohydrates and proteins (see Table 1)

TABLE 1

Results of analysis of components of extract of Grifola frondosa

| Item | Result | Method of analysis |
|---|---|---|
| Water | 2.0% | Heat-drying under reduced pressure |
| Protein | 38.1% | Kjeldahl method |
| Lipid | 0.1% | Acid hydrolysis method |
| Ash content | 9.6% | Direct ashing |
| Carbohydrate | 50.3% | |
| Energy | 354 kcal/100 g | |

Samples: Fractions having molecular weights of 30,000 to 100,000 [Analyzer: Japan Food Research Laboratories]

Amino acid composition of a protein: glutamic acid, aspartic acid, alanine, lysine, valine, arginine, threonine, glycine, serine, leucine, proline, isoleucine, phenylalanine, tyrosine, histidine, tryptophan, cystine, and methionine [Analyzer: Japan Food Research Laboratories].

Subsequently, the fractions having molecular weights of 100,000 or greater, the fractions having molecular weights of 30,000 to 100,000, the fractions having molecular weights of 30,000 or less, and unfractionated extracts obtained in Example 2 were used to perform an anti-influenza virus test.

Test Example

Examination of Anti-Influenza Virus Activity

Figure 1:
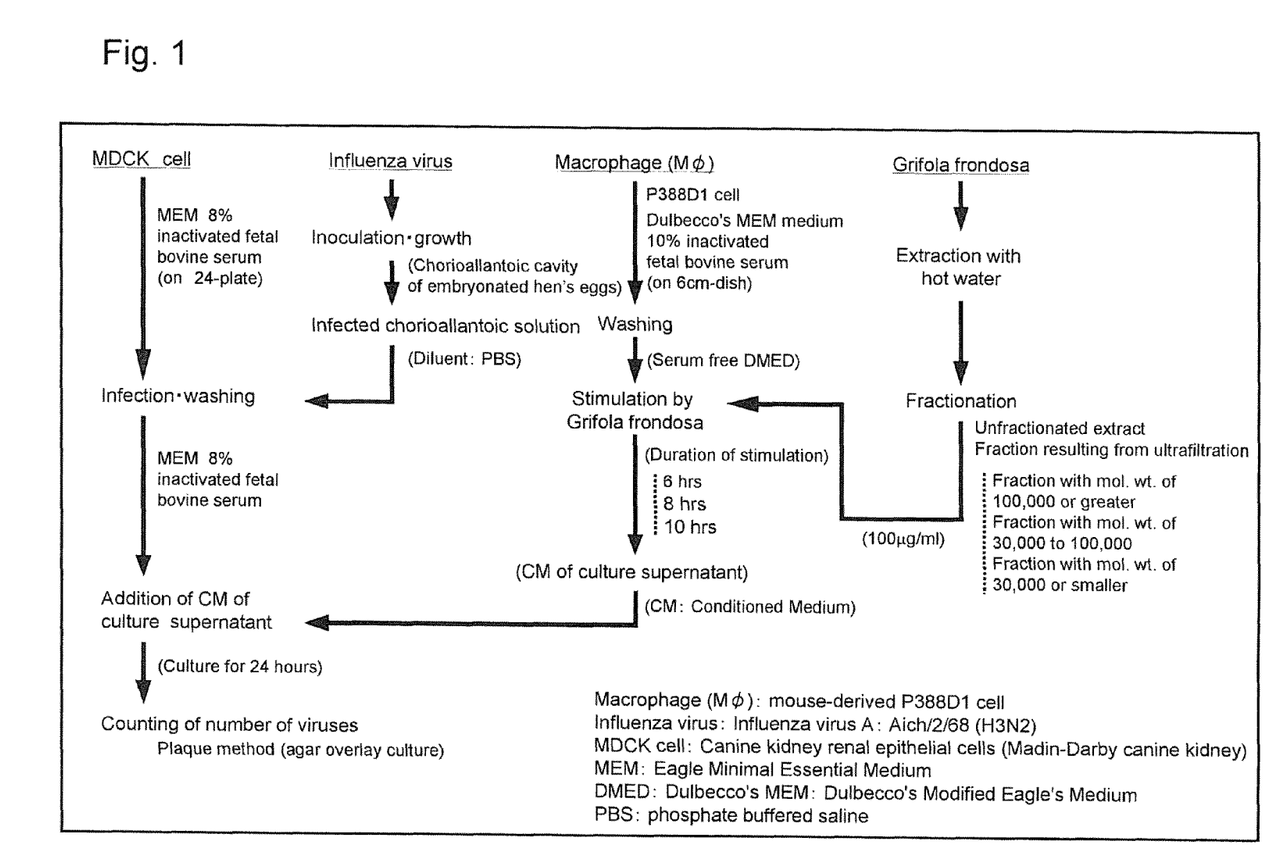
FIG. 1 shows a flow of the test of anti-influenza virus activity.

The entire procedure of complicated testing is summarized in FIG. 1.

Preparation of Materials

Materials used for the experiment for examination of anti-influenza virus activity are as shown below.

Test material-stimulating cells: Macrophage-derived P388D1 cells cultured in Dulbecco's MEM medium containing 10% inactivated fetal bovine serum were used.

Influenza virus-infected cells: MDCK cells cultured in MEM medium containing 8% inactivated fetal bovine serum were used.

Influenza virus: Influenza virus A/Aich/2/68 (H3N2). Viruses obtained by inoculating the chorioallantoic cavities of embryonated eggs with influenza viruses, designating the resulting infected chorioallantoic solution as an active virus solution, and adequately diluting the active virus solution with phosphate buffered saline were used.

Prior to the test, cytotoxicity of the extract of *Grifola frondosa* on the P388D1 cells was examined by the MTT method using mitochondrial enzyme activity as an index. When the P388D1 cells were stimulated with the extracts of *Grifola frondosa* obtained in Example 2 at various concentrations for 12 hours, no cytotoxicity was observed at concentrations of 200 μg/ml or lower. Based on such results, the extracts of *Grifola frondosa* obtained in Example 2 were used at 100 μg/ml in the following experiment.

Figure 2:
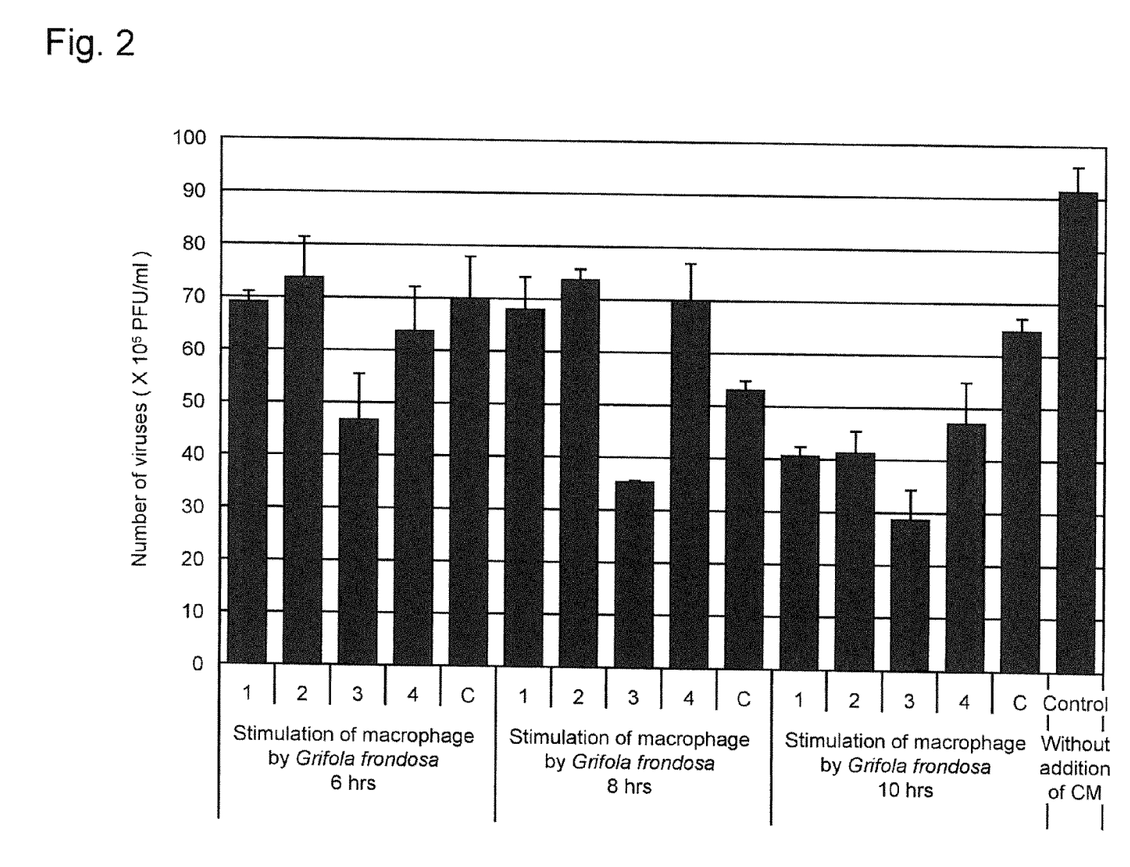
FIG. 2 shows a comparison of anti-influenza virus activities of *Grifola frondosa* extracts.

The fractions having molecular weights of 100,000 or greater, the fractions having molecular weights of 30,000 to 100,000, fractions having molecular weights of 30,000 or less, and unfractionated extracts obtained in Example 2 were subjected to a comparative test regarding anti-influenza virus activities (FIG. 2).

This comparative test was intended to examine the effects of the culture supernatant of *Grifola frondosa*-stimulated macrophage cells for inhibiting virus growth. The conditions of *Grifola frondosa* for stimulating macrophage cells (Mφ) were designated as follows.

1: Mφ was cultured without the addition of test materials. The CM thereof was added to the medium of infected cells.

2: Fractions having molecular weights of 100,000 or greater were added.

3: Fractions having molecular weights of 30,000 to 100,000 were added.

4: Fractions having molecular weights of 30,000 or less were added.

C: Unfractionated extracts were added.

Control: CM was not added.

The stimulatory effects of *Grifola frondosa* were assayed by adding the extracted fractions to Mφ, culturing the cells for given periods of time, adding the CM of the supernatants to MDCK cells that have been infected with viruses in advance, conducting culture, and counting the number of grown viruses (2 to 4 and C in FIG. 2).

As a comparative example 1, Mφ was cultured for given periods of time without the addition of the extract of *Grifola frondosa*, the CM supernatants thereof were added to the MDCK cells infected with viruses, culture was conducted, and the number of grown viruses was then counted (1 in FIG. 2).

As a control example 2, culture was conducted without the addition of any substance to the MDCK cells infected with viruses and the number of grown viruses was then counted (Control in FIG. 2).

As a conditioned medium (hereafter abbreviated to as "CM"), P388D1 cells cultured on a 6-cm dish in advance were washed once with serum-free DMED medium, the extracts of *Grifola frondosa* were added to the medium at 100 μg/ml, culture was conducted for given periods of time; i.e., stimulated by *Grifola frondosa* for 6, 8, and 10 hours, and the culture supernatant was adequately recovered and used as the CM. As a control, the CM culture supernatants that had been subjected to culture for the above periods of time without the addition of any extracts or extracted fractions (test materials) of *Grifola frondosa* were used.

Influenza viruses were sowed in MDCK cells that had been cultured on a 24-well plate at a multiplicity of infection (MOI) of 5 PFU/cell (5 virus particles per cell), the viruses were allowed to adsorb at room temperature for 60 minutes, and the plate was washed three times with phosphate buffered saline to remove nonadsorbed viruses by washing. Thereafter, CM was replaced with CM of other types (2 ml in general), culture was conducted for 12 hours, and the number of viruses grown in the MDCK cells was quantified by the plaque method. The result obtained via culture without the addition of CM was designated as the control. As a result, the condition 3 (i.e., fractions having molecular weights of 30,000 to 100, 000) was found to exhibit anti-influenza virus activity superior to other extracted fractions, among the groups stimulated with macrophages for 6, 8, and 10 hours, as shown in FIG. 2.

Figure 3:
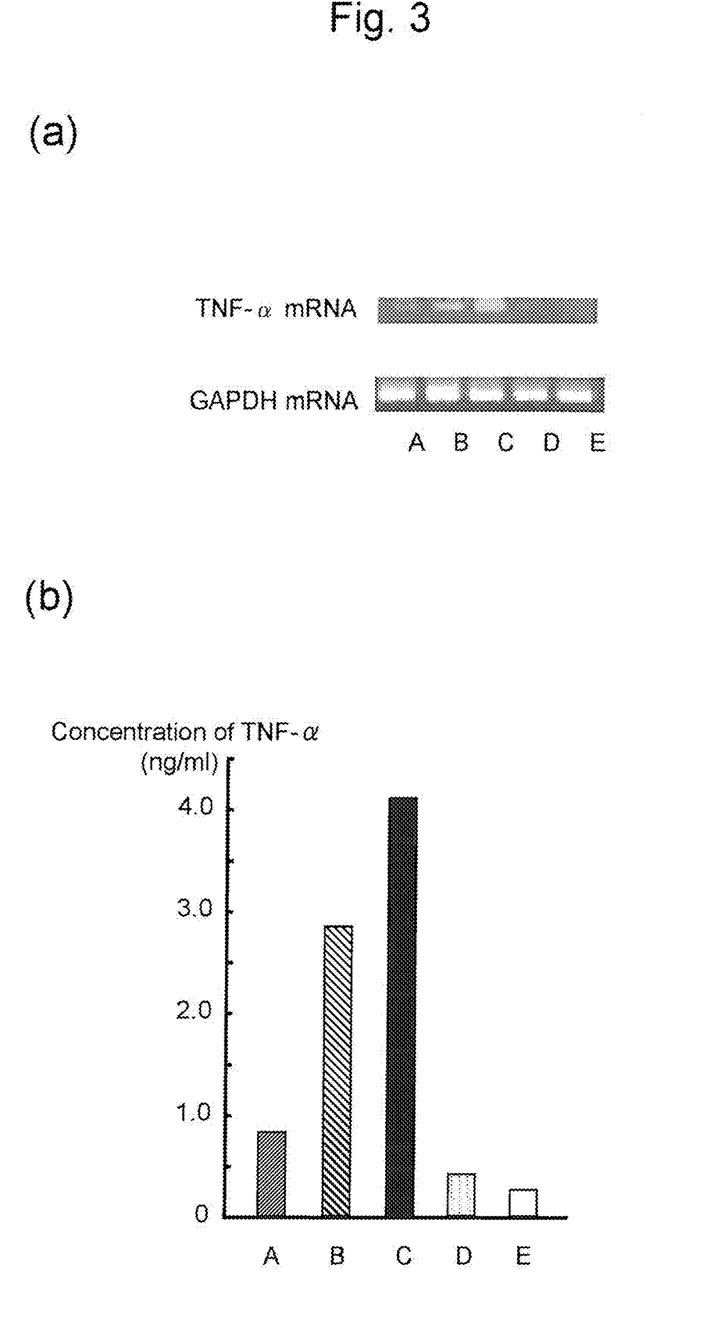
FIG. 3 shows influence of different fraction conditions of *Grifola frondosa* on macrophages.

FIG. 3 shows influence of different fraction conditions of *Grifola frondosa* on Mφ. FIG. 3(*a*) shows a comparison of the amount of TNF-α mRNA synthesized in Mφ via RT-PCR as a result of the addition of the unfractionated extracts, the fractions having molecular weights of 100,000 or greater, the fractions having molecular weights of 30,000 to 100,000, and the fractions having molecular weights of 30,000 or less obtained in Example 2 to various Mφ culture solutions.

The influence of Mφ (P388D1) on synthesis of TNF-α mRNA was inspected (RT-PCR) and stimulatory conditions of *Grifola frondosa* on Mφ were as follows.

A: Unfractionated extracts were added.

B: Fractions having molecular weights of 100,000 or greater were added.

C: Fractions having molecular weights of 30,000 to 100, 000 were added.

D: Fractions having molecular weights of 30,000 or less were added.

E: Test materials were not added.

The stimulatory effects of *Grifola frondosa* were assayed by adding the essences at 100 μg/ml to the Mφ medium (E was carried out without addition), conducting culture for 8 hours, and detecting TNF-αmRNA in Mφ via RT-PCR.

In the figure, GAPDH mRNA is mRNA of Mφ glyceraldehyde-3-phosphate dehydrogenase.

As a result, the fractions having molecular weights of 30,000 to 100,000 were found to accelerate expression of the TNF-α genes to the greatest extent. Also, unfractionated extracts and other fractions were found to have no influence on expression of the GAPDH internal standard genes that are constantly expressed.

FIG. 3(*b*) shows the results of the influence of different fraction conditions on production of TNF-α analyzed via ELISA.

The influence of Mφ (P388D1) on production of TNF-α mRNA was inspected (via ELISA) and stimulatory conditions of *Grifola frondosa* on Mφ were as follows.

A: Unfractionated extracts were added.

B: Fractions having molecular weights of 100,000 or greater were added.

C: Fractions having molecular weights of 30,000 to 100, 000 were added.

D: Fractions having molecular weights of 30,000 or less were added.

E: Test materials were not added.

The stimulatory effects of *Grifola frondosa* were assayed by adding the essences at 100 mg/ml to the Mφ medium (E was carried out without addition), conducting culture for 8 hours, and assaying the amount of TNF-α in the culture supernatant via ELISA.

As a result, the fractions having molecular weights of 30,000 to 100,000 were found to produce the greatest amount of TNF-α in Mφ.

Figure 4:
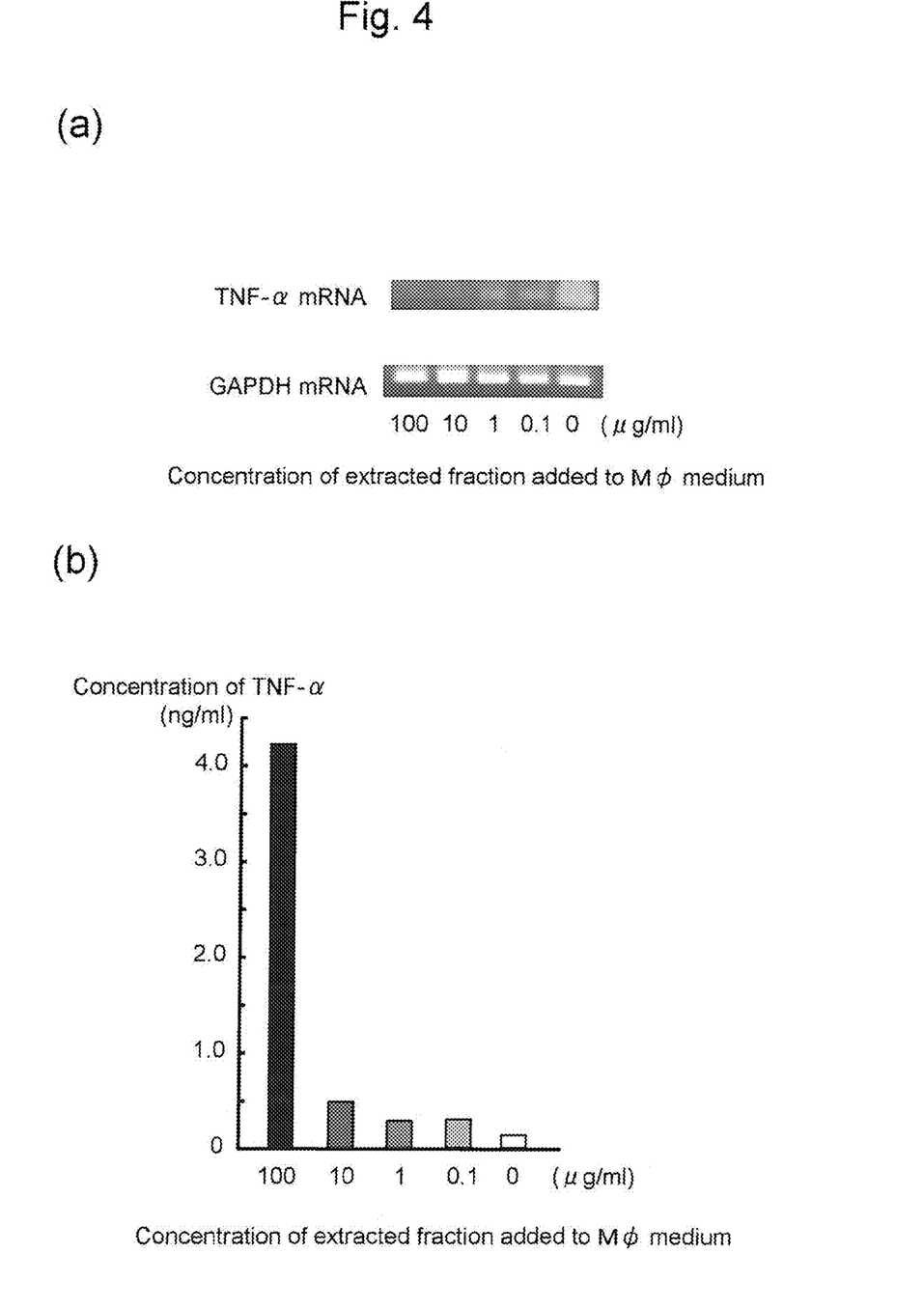
FIG. 4 shows influence of concentrations of fractions extracted from *Grifola frondosa* on macrophages for the production of TNF-α.

FIG. 4 shows influence of the addition of fractions having molecular weights of 30,000 to 100,000 extracted from *Grifola frondosa* to the Mφ medium while varying the concentrations of the fractions. FIG. 4(*a*) shows the results of detecting TNF-α mRNA transcribed in Mφ cells via RT-PCR.

The effects of Mφ (P388D1) on synthesis of TNF-α mRNA were assayed (via RT-PCR). The stimulatory effects of *Gri-* fola frondosa were assayed by adding the fractions having molecular weights of 30,000 to 100,000 at various concentrations to the Mφ medium, conducting culture for 8 hours, and detecting TNF-α mRNA in Mφ via RT-PCR.

In the figure, GAPDH mRNA is mRNA of Mφ glyceraldehyde-3-phosphate dehydrogenase.

For the purpose of comparison, the results of detecting mRNA of glyceraldehyde-3-phosphate dehydrogenase (GAPDH), which is known to be constantly expressed as an internal standard gene, are shown. As a result, the amount of TNF-α mRNA transcribed was found to increase in a concentration-dependent manner in response to stimulation by Grifola frondosa. However, it was found to have no influence on expression of constantly expressed GAPDH.

FIG. 4(b) shows the results of assaying the amount of TNF-α produced in Mφ cells via ELISA. The effects of Mφ (P388D1) on production of TNF-α were assayed (via ELISA). The stimulatory effects of Grifola frondosa were assayed by adding the fractions having molecular weights of 30,000 to 100,000 at various concentrations to the Mφ medium, conducting culture for 8 hours, and assaying the amount of TNF-α in the culture supernatant via ELISA.

As a result, the amount of TNF-α produced was found to increase in a concentration-dependent manner in response to stimulation by Grifola frondosa.

INDUSTRIAL APPLICABILITY

Grifola frondosa-derived fractions having molecular weights of 30,000 to 100,000 were found to have activities of stimulating macrophages to induce TNF-α synthesis and to have anti-influenza virus activity. Thus, such fractions can be used for food products, pharmaceutical products, and feeds or feed additives for prevention of the common cold, such as influenza, or for alleviation of symptoms after infection.

All publications, patents, and patent applications cited herein are incorporated herein by reference in their entirety.

The invention claimed is:

1. A fraction extracted from Grifola produced by a method comprising extracting the fruit body or mycelia of Grifola with hot water, treating the resulting extract with a molecular sieve apparatus to obtain a fraction, wherein
the fraction has a molecular weight distribution of 30,000 to 100,000, comprises sugar and protein at a ratio of 50:50 to 65:35, respectively, and has positive reactions with anthrone and ninhydrin.

2. An active substance for inducing TNF-α production comprising the fraction extracted from Grifola according to claim 1.

3. A substance having anti-influenza virus activity comprising the fraction extracted from Grifola according to claim 1.

4. A food and beverage product comprising the fraction extracted from Grifola according to claim 1.

5. A pharmaceutical product comprising the fraction extracted from Grifola according to claim 1.

6. A feed or feed additive comprising the fraction extracted from Grifola according to claim 1.

7. A fraction extracted from Grifola produced by a method comprising extracting the fruit body or mycelia of Grifola with hot water, adding alcohol to the resulting extract to form a liquid mixture, allowing the liquid mixture to stand, removing substances suspended on the surface of the liquid mixture or in the liquid mixture, treating the liquid mixture with a molecular sieve apparatus to obtain a fraction, wherein
the fraction has a molecular weight distribution of 30,000 to 100,000, comprises sugar and protein at a ratio of 50:50 to 65:35, respectively, and has positive reactions with anthrone and ninhydrin.

* * * * *